(12) United States Patent
Hirota et al.

(10) Patent No.: US 8,765,633 B2
(45) Date of Patent: Jul. 1, 2014

(54) CATALYST FOR PRODUCTION OF ETHYLENE OXIDE AND METHOD FOR PRODUCTION OF ETHYLENE OXIDE

(75) Inventors: Hiroyuki Hirota, Hyogo (JP); Hiromi Yunoki, Hyogo (JP); Kenichi Ochiai, Hyogo (JP)

(73) Assignee: Nippon Shokubai Co., Ltd. (JP)

( * ) Notice: Subject to any disclaimer, the term of this patent is extended or adjusted under 35 U.S.C. 154(b) by 480 days.

(21) Appl. No.: 13/070,087

(22) Filed: Mar. 23, 2011

(65) Prior Publication Data

US 2011/0245518 A1 Oct. 6, 2011

(30) Foreign Application Priority Data

Mar. 31, 2010 (JP) ................................ 2010-084467

(51) Int. Cl.
*B01J 23/58* (2006.01)
*B01J 23/48* (2006.01)
*C07D 301/10* (2006.01)
*C07D 301/03* (2006.01)

(52) U.S. Cl.
USPC ............ 502/347; 502/330; 549/536; 549/534

(58) Field of Classification Search
USPC .......................... 502/330, 347; 549/536, 534
See application file for complete search history.

(56) References Cited

U.S. PATENT DOCUMENTS

| 5,734,068 A * | 3/1998 | Klopries et al. .............. 549/536 |
| 6,304,470 B1 | 10/2001 | Isago et al. |
| 7,547,795 B2 | 6/2009 | Matusz et al. |
| 7,850,928 B2 | 12/2010 | Tanimoto et al. |
| 2002/0136678 A1 | 9/2002 | Tanimoto et al. |
| 2007/0037704 A1 | 2/2007 | Rizkalla |

FOREIGN PATENT DOCUMENTS

| JP | 2002-306953 A | 10/2002 |
| JP | 2007-500596 T | 1/2007 |
| JP | 2010-036115 | 2/2010 |
| RU | 2169040 C2 | 6/2001 |
| WO | 2008064076 A2 | 5/2008 |

* cited by examiner

*Primary Examiner* — T. Victor Oh

(74) *Attorney, Agent, or Firm* — Fox Rothschild LLP; Peter J. Butch, III; Robert N. Henrie, II

(57) ABSTRACT

A catalyst for the production of ethylene oxide in high efficiency and high selectivity, as well as stably for a long period of time is provided.

A catalyst for the production of ethylene oxide comprising silver and a reaction promoter supported on a porous carrier comprising α-alumina as a main component, characterized in that a relative standard deviation of silver supporting rate of each particle of the catalyst is 0.001 or more and 0.1 or less.

4 Claims, No Drawings

CATALYST FOR PRODUCTION OF ETHYLENE OXIDE AND METHOD FOR PRODUCTION OF ETHYLENE OXIDE

CROSS-REFERENCE TO RELATED APPLICATIONS

This application claims priority benefit under 35 U.S.C. §120 of Japan Patent Application No. 2010-084467 filed Mar. 31, 2010, the disclosure of which is incorporated herein by reference.

BACKGROUND OF THE INVENTION

1. Field of the Invention

This invention relates to a catalyst for the production of ethylene oxide and a method for the production of ethylene oxide. In more detail, this invention relates to a catalyst for the production of ethylene oxide superior in selectivity of ethylene oxide and catalyst life, and is capable of producing ethylene oxide in high selectivity for a long period of time, and a method for the production of ethylene oxide using this catalyst for the production of ethylene oxide.

2. Description of the Related Art

It has been widely performed industrially to produce ethylene oxide by catalytic vapor phase oxidation of ethylene with a molecular oxygen-containing gas in the presence of a silver catalyst. As for the silver catalyst to be used in this catalytic vapor phase oxidation, various technologies have been proposed on a carrier thereof, a supporting method, and a reaction promoter or the like.

Catalytic activity, selectivity and catalyst life of the silver catalyst have reached a high level already, however, still more enhancement of catalytic performance thereof has been required. For example, as for selectivity, because of a large production scale of ethylene oxide, even only 1% of enhancement of selectivity provides extreme saving of use amount of ethylene as law material, and economical effect thereof is large. Under such circumstance, development of the silver catalyst having more superior catalytic performance and pursuit of high efficiency or enhancement of selectivity of catalytic vapor phase oxidation reaction in a multi-tube type reactor using the same have been continuous themes of researchers in the relevant technical field.

For example, WO 2004/101144 discloses a catalyst having silver supported on a carrier having α-alumina as a main component, and describes about suitable catalyst size, amount of silver supported, as well as amount of silver loaded in a catalyst layer obtained by packing the catalyst in a reactor. In addition, for example, JP-A-2002-306953 describes that a catalyst can be packed uniformly and used stably for a long period of time by packing the catalyst in a reaction tube of a fixed-bed multi-tube type reactor at a prescribed rate. Further, for example, JP-A-2010-36115 discloses a method for packing a catalyst having a prescribed outer diameter or length into a reaction tube having a prescribed inner diameter, and describes about amount of silver contained in the catalyst layer.

SUMMARY OF THE INVENTION

However, there is room for improvement in the point that conversion and selectivity of reaction remain at insufficient levels even using the methods described in the patent literatures mentioned above. In addition, although development of a catalyst for the production of ethylene oxide which is capable of sufficiently satisfying both of selectivity of the catalyst and life of the catalyst has been demanded, but has not been realized still yet.

Accordingly, it is an object of this invention to provide a catalyst for the production of ethylene oxide, which is capable of stably producing ethylene oxide in high efficiency and high selectivity for a long period of time.

In addition, it is another object of this invention to provide a method for the production of ethylene oxide using this catalyst.

We have intensively studied a way to solve the above-described problem, in particular, about distribution of supporting rate of silver contained in the catalyst for the production of ethylene oxide. As a result, we have found that in the catalyst comprising silver and a reaction promoter supported on a porous carrier comprising α-alumina as a main component, a desired performance cannot be obtained when content (supporting rate) of silver contained in each catalyst particle is uneven. Furthermore, we have also found that by supporting silver uniformly on a porous carrier comprising α-alumina as a main component, ethylene oxide can be produced in higher efficiency and higher selectivity and also catalyst life is longer compared with those of the case when silver is supported under the conditions other than the above, and thus accomplished this invention.

That is, this invention is a catalyst for the production of ethylene oxide comprising silver and a reaction promoter supported on a porous carrier comprising α-alumina as a main component, characterized in that a relative standard deviation of silver supporting rate of each particle of the catalyst determined by the following formula (1) is 0.001 or more and 0.1 or less.

$$\text{(Relative standard deviation of silver supporting rate)} = \frac{\text{(Standard deviation of silver supporting rate)}}{\text{(Average silver supporting rate)}} \quad (1)$$

wherein the standard deviation of silver supporting rate is determined by the following formula (2):

$$\text{(Standard deviation of silver supporting rate)} = \sqrt{\frac{N\sum Xn^2 - (\sum Xn)^2}{N(N-1)}} \quad (2)$$

(wherein N represents the number of catalyst particles for which the silver supporting rate is measured, and Xn represents the silver supporting rate of each particle); and the average silver supporting rate is an arithmetic mean of the silver supporting rates of N particles.

In addition, this invention is a method for the production of ethylene oxide which comprises subjecting ethylene to catalytic vapor phase oxidation with a molecular oxygen-containing gas in the presence of the catalyst for the production of ethylene oxide.

The catalyst for the production of ethylene oxide of this invention can be suitably used as a catalyst for the production of ethylene oxide using a fixed-bed multi-tube type reactor, and exhibits high efficiency and high selectivity, as well as superior catalyst life (durability). For this reason, by using the catalyst of this invention, ethylene oxide can be produced stably for a long period of time.

DETAILED DESCRIPTION OF THE PREFERRED EMBODIMENTS

Explanation will be given below on embodiments of this invention.

An aspect of this invention is a catalyst for the production of ethylene oxide comprising silver and a reaction promoter supported on a porous carrier comprising or α-alumina as a main component, characterized in that a relative standard deviation of silver supporting rate of each particle of the catalyst is 0.001 or more and 0.1 or less.

The relative standard deviation of silver supporting rate is a value determined by the following formula (1).

$$\text{(Relative standard deviation of silver supporting rate)} = \frac{\text{(Standard deviation of silver supporting rate)}}{\text{(Average silver supporting rate)}} \quad (1)$$

wherein the standard deviation of silver supporting rate is determined by the following formula (2):

$$\text{(Standard deviation of silver supporting rate)} = \sqrt{\frac{N\sum Xn^2 - (\sum Xn)^2}{N(N-1)}} \quad (2)$$

(wherein N represents the number of catalyst particles for which the silver supporting rate is measured, and Xn represents the silver supporting rate of each particle); and the average silver supporting rate is an arithmetic mean of the silver supporting rates of N particles.

A composition of the carrier to be used for the catalyst for the production of ethylene oxide of this invention is not especially limited, as long as it comprises α-alumina as a main component. Here, the carrier "comprises α-alumina as a main component" means that it may contain partially alumina of different form other than α-alumina, such as, γ-alumina, amorphous alumina. Content of alumina in the carrier is preferably equal to or higher than 90% by mass, more preferably equal to or higher than 95% by mass, and still more preferably equal to or higher than 98% by mass relative to the total mass, 100% by mass, of the carrier. Other composition is not especially limited, as long as it is one comprising α-alumina as a main component, however, the carrier may include, for example, an oxide of an alkali metal or an alkaline earth metal, or an oxide of a transition metal. The content thereof is also not especially limited, however, the content of the oxide of the alkali metal or the alkaline earth metal is preferably 0 to 5% by mass, and more preferably 0.01 to 4% by mass, as converted to an oxide. In addition, the content of the oxide of the transition metal is preferably 0 to 5% by mass, and more preferably 0.01 to 3% by mass, as converted to an oxide.

In addition, the carrier usually contains silica (silicon dioxide). Content of silica in the carrier is not especially limited, however, preferably 0.01 to 10.0% by mass, more preferably 0.1 to 5.0% by mass, and still more preferably 0.2 to 3.0% by mass.

It should be noted that, the composition of the above carrier or the content of each component may be determined using X-ray fluorescence analysis method.

Particle diameter of an α-alumina as a raw material of the carrier, is not especially limited, however, a primary particle diameter of the α-alumina is preferably 0.01 to 100 μm, more preferably 0.1 to 20 μm, still more preferably 0.5 to 10 μm, and particularly preferably 1 to 5 μm. In addition, secondary particle diameter of the α-alumina is preferably 0.1 to 1,000 μm, more preferably 1 to 500 μm, still more preferably 10 to 200 μm, and particularly preferably 30 to 100 μm.

Shape of the carrier is not particularly limited, and besides ring shape, spherical shape, cylindrical shape, pellet shape, and shape of hollow cylinder, conventionally known knowledge can be appropriately referred to. In addition, size (mean diameter) of the carrier is not particularly limited, however, preferably 3 to 20 mm, and more preferably 4 to 10 mm.

Specific surface area of the carrier is also not especially limited, however, preferably 0.03 to 10 m$^2$/g, more preferably 0.3 to 5.0 m$^2$/g, and still more preferably 0.5 to 3.0 m$^2$/g. When specific surface area of the carrier is equal to or higher than 0.03 m$^2$/g, support of necessary amount of catalyst component becomes possible, and as the specific surface area of the carrier becomes greater, highly dispersed support of the catalyst component becomes easier. In addition, the specific surface area of equal to or higher than 0.03 m$^2$/g is preferable, because surface area of the catalyst component, which is an active site of catalytic reaction, becomes larger. On the other hand, when the specific surface area of the carrier is equal to or lower than 10 m$^2$/g, pore diameter of the carrier can be maintained at a certain level of large value, and sequential oxidation of ethylene oxide during the production of ethylene oxide using the catalyst obtained can be repressed. It should be noted that, as a value of the specific surface area of the carrier, a value obtained by a method described in Examples to be described later is adopted.

Preferably the carrier has a crush strength of at least 40N. The crush strength of the carrier is preferably equal to or higher than 50 N, and more preferably equal to or higher than 60N. The crush strength within the above range is capable of maintaining sufficient mechanical strength. The upper limit value of the crush strength of the carrier is not especially limited. It should be noted that, as a value of the crush strength of the carrier, a value obtained by a method described in Examples to be described later is adopted.

The bulk density of the carrier is preferably 0.5 to 1.0 kg/L, more preferably 0.5 to 0.9 kg/L, and still more preferably 0.5 to 0.80 kg/L. The bulk density of the carrier within the above range is capable of providing a suitable packing density and thus producing a catalyst with sufficient strength. It should be noted that, as for a value of the bulk density of the carrier, a value obtained by a method described in Examples to be described later is adopted.

A pore volume of the carrier is also not especially limited, however, preferably 0.2 to 0.6 cm$^3$/g, and more preferably 0.3 to 0.5 cm$^3$/g. The pore volume of the carrier of equal to or larger than 0.2 cm$^3$/g is preferable in view of making supporting of the catalyst component easy. On the other hand, the pore volume of the carrier of equal to or smaller than 0.6 cm$^3$/g is preferable in view of securing strength of the carrier in a practical level. It should be noted that, as a value of the pore volume of the carrier, a value obtained by Mercury Porosimetry is adopted.

A pore size which the carrier has is also not especially limited, however, a median pore diameter is preferably 0.1 to 10 μm, more preferably 0.2 to 4.0 μm, and still more preferably 0.3 to 3.0 μm. The median pore diameter of equal to or larger than 0.1 μm is capable of repressing sequential oxidation of ethylene oxide accompanying with residence of generated gas in producing ethylene oxide. On the other hand, the median pore diameter of equal to or smaller than 10 μm is capable of securing strength of the carrier in a practical level.

It should be noted that, as a value of the median pore diameter, a value obtained by Mercury Porosimetry is adopted.

A water absorption of the carrier is also not especially limited, however, preferably 10 to 70%, more preferably 20 to 60%, and still more preferably 30 to 50%. The water absorption of the carrier of equal to or higher than 10% makes supporting of the catalyst component easy. On the other hand, the water absorption of the carrier of equal to or lower than 70% is capable of securing strength of the carrier in a practical level. It should be noted that, as a value of the water absorption of the carrier, a value obtained by a method described in Examples to be described later is adopted.

A wear rate of the carrier is preferably equal to or lower than 5.0%, more preferably equal to or lower than 4.0%, still more preferably equal to or lower than 3.0%, and particularly preferably equal to or lower than 2.0%. The wear rate of equal to or lower than 5.0% is advantageous in view of equipment and utility, because cracking and pulverization of the catalyst in packing of the catalyst into a reaction tube are difficult to occur and pressure loss is low. It should be noted that, as a value of the wear rate of the carrier, a value obtained by a method described in Examples to be described later is adopted.

The catalyst for the production of ethylene oxide of this invention has a constitution comprising silver as a catalyst component supported on the above carrier. In addition, a catalyst component to be used generally as a reaction promoter may be supported on the carrier, other than silver. A typical example of the reaction promoter includes an alkali metal, specifically lithium, sodium, potassium, rubidium and cesium or the like. Other than an alkali metal, thallium, sulfur, chromium, molybdenum, tungsten, rhenium or the like may also be used as the reaction promoter. These reaction promoters may be used alone as one kind, or two or more kinds may be used in combination. Among these, cesium may be used suitably used as the reaction promoter.

In the catalyst of this invention, silver and a reaction promoter are supported on a porous carrier comprising α-alumina as a main component. Here, silver and the reaction promoter may be supported so that relative standard deviation of supporting rate of silver contained in each catalyst particle determined by the above formula (1) for N catalyst particles becomes 0.001 or more and 0.1 or less. The relative standard deviation is more preferably 0.001 or more and 0.05 or less, still more preferably 0.001 or more and 0.03 or less, and particularly preferably 0.001 or more and 0.02 or less. When the relative standard deviation of silver supporting rate exceeds 0.1, selectivity and stability of catalyst life are reduced due to increased variation of silver content. It should be noted that, the number of catalyst particles N to be used for measurement of the silver supporting rate is equal to or larger than 30.

Supporting rate of silver or the reaction promoter is not especially limited so long as the relative standard deviation of silver supporting rate is within the above range, and silver or the reaction promoter may be supported in an amount effective in producing ethylene oxide, respectively. For example, in the case of silver, an average supporting rate thereof of N catalyst particles is 1 to 30% by mass, and preferably 5 to 20% by mass, based on mass of the catalyst for the production of ethylene oxide. In this case, the value of the average silver supporting rate (relative to the mass of the catalyst) is given by an arithmetic mean of the silver supporting rates of N catalyst particles. In addition, the supporting rate of the reaction promoter is usually 0.001 to 2% by mass, preferably 0.01 to 1% by mass, and more preferably 0.01 to 0.7% by mass, based on mass of the catalyst for the production of ethylene oxide. In particular, optimal supporting rate of the reaction promoter is different depending on difference of property of the carrier or a combination of the reaction promoters. Therefore, it is preferable that catalysts with different supporting rates of the reaction promoter are prepared in advance, and after performance evaluation of the relevant catalysts, the supporting rate of the reaction promoter showing the highest performance is determined and amount of the reaction promoter showing such highest performance is supported, and thus the catalyst is prepared. It should be noted that, in the following Examples and Controls, the catalyst was prepared after determining the supporting rate of the reaction promoter showing the highest performance in advance, in this way.

The catalyst for the production of ethylene oxide of this invention may be prepared according to a conventionally known production method for preparing a catalyst for the production of ethylene oxide.

Explanation will be given below on one example of a method for producing a catalyst for the production of ethylene oxide of this invention using the above-described carrier, however, the technical scope of this invention should be determined based on description of claims, and should not be limited to only the following method.

Firstly, the carrier is prepared. As for a preparation method for the carrier, it has been known that by adopting the following preparation method, size or property of the carrier can be controlled. That is, 1) a method for adding a pore forming agent with a desired size and amount into a parent powder having α-alumina as a main component, 2) a method for formulating at least two kinds of parent powders having different property in a desired mixing ratio, and 3) a method for calcining the carrier at desired temperature for desired time or the like, and a method by combining them has also been known. For example, to the α-alumina, a molding auxiliary agent having effect for enhancing moldability, a reinforcing agent or a binder for enhancing strength of the catalyst, and a pore forming agent for forming fine pores to the catalyst are added and mixed. As a substance to be added, one not to give bad influence on catalytic performance by the addition is preferable. For example, an inorganic binder such as silica, alumina, silica-alumina, glass fiber, silicon carbide, silicon nitride, graphite may be added. An organic binder such as ethylene glycol, glycerin, propionic acid, maleic acid, benzyl alcohol, propyl alcohol, butyl alcohol, cellulose, methylcellulose, starch, polyvinyl alcohol or phenol is added as needed. In addition, a shell or a seed of a peach, an apricot, a chestnut or the like with uniform particle diameter or a substance with uniform particle diameter, which disappears by calcining, may be added as the pore forming agent. After sufficient mixing using a mixing machine such as a kneader by further adding water, it is molded into desired shape using a suitable mold by extrusion molding or the like, granulated, dried and then calcined. These preparation methods are described, for example, in "Property of porous substances and application technology thereof" edited by Yoh Takeuchi, and issued by Fujitec Corporation (1999). In addition, JP-A-5-329368, JP-A-2001-62291, JP-A-2002-136868, JP-B-2983740, JP-B-3256237, JP-B-3295933 or the like may also be referred.

Meanwhile, a solution for making silver supported on the carrier is prepared. Specifically, a silver compound alone, or together with a complexing agent for forming a silver complex or a compound containing a reaction promoter as needed, is added to a solvent such as water, methanol, and ethanol. As the solvent, water is preferable.

Here, a silver compound includes, for example, silver nitrate, silver carbonate, silver oxalate, silver acetate, silver propionate, silver lactate, silver citrate, silver neodecanoate or the like. Among these, silver oxalate and silver nitrate are preferable. In addition, a complexing agent includes, for example, monoethanolamine, diethanolamine, triethanolamine, ethylenediamine, propylenediamine or the like. These silver compounds or complexing agents may be used alone as only one kind, or two or more kinds may be used in combination. Addition amount of the silver compound can be determined appropriately so as to become the above-described prescribed average supporting rate.

Next, the carrier obtained above is impregnated with or clipped into the solution also obtained above. In this step, the reaction promoter may be impregnated simultaneously by dissolving a compound containing the reaction promoter into a solution containing the silver compound prior to the step when the carrier is impregnated with or dipped into the solution, or may be supported after silver is supported. Preferably, the reaction promoter is impregnated simultaneously by dissolving it into the solution containing the above silver compound. When cesium is used as the reaction promoter, nitrate salt, nitrite salt, carbonate salt, oxalate salt, halide, acetate salt, sulfate salt, perrhenate salt, molybdate salt and the like of cesium can be preferably used. Among these, cesium nitrate, cesium perrhenate and cesium molybdate are particularly preferable. When molybdenum is used as the reaction promoter, molybdenum oxide, molybdic acid, molybdate salt, as well as heteropoly acid such as silicomolyblic acid, phosphomolybdic acid, and/or heteropoly acid salt, and the like can be preferably used. Among these, ammonium paramolybdate, cesium paramolybdate, ammonium phosphomolybdate, cesium phosphomolybdate, ammonium silicomolybdate and cesium silicomolybdate are particularly preferable. These compounds containing the reaction promoter may be used alone or in combination of two or more kinds.

In this invention, in order to support the catalyst component so that the relative standard deviation of the supporting rate of silver contained in each catalyst particle becomes 0.001 or more and 0.1 or less, preferably the carrier prepared above is impregnated with the above solution under stirring, for example, using a blender. As a blender to be used for impregnating the above solution, for example, V type, double-corn type, spherical type, cylinder type, and the like can be used. For the purpose to impregnate the liquid homogeneously, a blender which has, in addition to the structures described above, a mixing system such as revolution, rocking, and the like to improve mixing efficiency of the solution and the carrier is preferably used. Even when the carrier is impregnated with the solution by clipping, the absorbed solution is dried after once coming out from the carrier with heating, and silver is sometimes supported unevenly. In order to prevent such uneven support, a blender having a structure and a revolution system which is capable of achieving superior mixing efficiency is preferably used.

The revolution rate (number of revolutions) varies depending on shape and volume of the treatment container, the carrier and the solution to be charged, however, is generally set at 0.1 to 20 rpm, preferably 0.1 to 15 rpm, and further more preferably 0.1 to 10 rpm. When the revolution rate is equal to or higher than 0.1 rpm, a high stirring efficiency can be obtained. When the revolution rate is equal to or lower than 20 rpm, such a problem hardly occurs that the carrier is pulverized by repeated collisions. In addition, when a container capable of rocking is used, the rocking rate is set, for example, at 1 to 12 spm, preferably at 1 to 10 spm, and further more preferably at 1 to 5 spm. In this case, unit of spm represents number of repetitions of rocking per minute provided that one repetition of rocking action is 1. When the rocking rate is equal to or higher than 1 spm, effect of rocking is high. When the rocking rate is equal to or lower than 12 spm, high mixing efficiency can be obtained, because content of the container sufficiently migrates toward the axis of revolution before the container tilts toward the reverse direction, and migration of the content toward the axis of revolution efficiently progresses. Furthermore, the maximum range of tilt angle of the container from the axis of revolution is preferably 5° or more. The container may also revolve. The maximum range of the tilt angle of the container from the axis of revolution of 5° or more is capable of improving the effect of mixing efficiency by rocking.

Subsequently, it is dried and calcined. The drying is preferably performed in atmosphere of air, oxygen or an inert gas (for example, nitrogen), at a temperature of 80 to 120° C. In addition, the calcining is preferably performed in atmosphere of air, oxygen, overheated steam or an inert gas (for example, nitrogen), at a temperature of 150 to 700° C., and preferably 200 to 600° C. It should be noted that, the calcining may be performed in one stage only or may be performed in two stages or more. Preferable calcining condition includes to perform the first stage calcining in air atmosphere at 150 to 250° C. for 0.1 to 10 hours, and to perform the second stage calcining in air atmosphere at 250 to 450° C. for 0.1 to 10 hours. Still more preferably, after such two stages of calcining, the third stage calcining may be performed under the atmosphere of an inert gas (for example, nitrogen, helium, argon or the like) at 450 to 700° C. for 0.1 to 10 hours.

It should be noted that, as content (silver supporting rate) of silver contained in each particle of the catalyst obtained by the above method, a value analyzed by the method described in Examples is adopted.

Another aspect of this invention is a method for the production of ethylene oxide which comprises subjecting ethylene to catalytic vapor phase oxidation with a molecular oxygen-containing gas in the presence of the catalyst for the production of ethylene oxide.

The method for the production of ethylene oxide of this invention is performed in accordance with a usual method, except that the catalyst for the production of ethylene oxide of this invention is used as a catalyst. For example, a method, in which ethylene is subjected to catalytic vapor phase oxidation with a molecular oxygen-containing gas such as air, oxygen and oxygen-enriched air, using a reactor for producing ethylene oxide with a reaction tube packed with the catalyst for the production of ethylene oxide, can be used.

The reactor for producing ethylene oxide to be used in this invention may be either a single-tube type reactor or a multi-tube type reactor, however, a multi-tube type reactor having multiple reaction tubes can be preferably used for industrial purpose. The reactor for producing ethylene oxide is not particularly limited, and conventionally known reactor such as fixed-bed reactor, fluidized bed reactor, moving bed reactor can be used, but preferably fixed-bed reactor, and particularly preferably fixed-bed multi-tube type reactor is used. As the reaction tube of the reactor for producing ethylene oxide, the one having an inner diameter of preferably 15 to 50 mm is used. The inner diameter of the reaction tube is more preferably 18 to 45 mm, and furthermore preferably 20 to 40 mm. When the inner diameter of the reaction tube is 15 mm or more, manufacturing cost of the reactor can be held down because the number of the reaction tube does not increase excessively. Meanwhile, when the inner diameter of the reaction tube is 50 mm or less, heat removal effect is improved and heat accumulation in a catalyst layer hardly occurs.

In the reactor for producing ethylene oxide to be used in this invention, the catalyst for the production of ethylene oxide has a value of outer diameter or length, whichever is larger, of preferably 10 to 50%, more preferably 15 to 45%, and still more preferably 20 to 40%, relative to the inner diameter of the reaction tube. When the value of outer diameter or length, whichever is larger, of the catalyst is 10% or more relative to the inner diameter of the reaction tube, the reaction is advantageous from the both points of equipment and utility because packing density and pressure loss become low. Meanwhile, when the value of outer diameter or length, whichever is larger, of the catalyst is 50% or less relative to the inner diameter of the reaction tube, activity and life of the catalyst can be improved because silver content in the catalyst layer becomes high.

In addition to the above-described conditions, by packing the catalyst so that content of silver as a catalyst component to be contained in a catalyst layer becomes 30 to 140 kg/m$^3$, activity and life of the catalyst is improved. In addition, packing density is adjusted by controlling the packing rate, by which content of silver to be contained in the catalyst layer can be easily adjusted.

When the content of silver to be contained in the catalyst layer is 140 kg/m$^3$ or less, the reaction is advantageous from the both points of equipment and utility because packing density and pressure loss become low. Meanwhile, when the content of silver to be contained in the catalyst layer is 30 kg/m$^3$ or more, silver content in the catalyst layer becomes high and activity and life of the catalyst can be improved. The content of silver to be contained in the catalyst layer is more preferably 60 to 135 kg/m$^3$, and further more preferably 100 to 130 kg/m$^3$. As a value of the content of silver to be contained in the catalyst layer, a value calculated by the following formula (3) is adopted. Here, the packing density when the catalyst is packed in a reaction tube is calculated by formula (5) to be described below. In addition, as an average silver supporting rate, a value analyzed by a method described in Examples is adopted.

Content of silver in the catalyst layer (kg/cm$^3$)=[(Average silver supporting rate(% by mass)/100)× Packing density (kg/L)]×1000 (3)

Preferably, in order to control the content of silver to be contained in the catalyst layer, the catalyst for the production of ethylene oxide described above is packed in the above reaction tube at a packing rate of 0.3 to 5 L/min. The packing rate is more preferably 0.5 to 4 L/min, and further more preferably 1.0 to 3.0 L/min. By controlling the packing rate in a range of 0.3 to 5 L/min, activity and life of the catalyst are improved and ethylene oxide can be produced in high efficiency and high selectivity, because the catalyst layer containing an appropriate amount of the catalyst component is formed. As a value of the packing rate, the value calculated by measuring packing time required when the catalyst is packed in a reaction tube having a desired inner diameter, and the length of a catalyst packed layer; and calculating the value by the following formula (4) is adopted.

Packing rate (L/min)=Packed volume of the catalyst (L)/Packing time of the catalyst (min) (4)

In this invention, the catalyst for the production of ethylene oxide is preferably packed in a reaction tube of the reactor for producing polyethylene oxide so that a packing density becomes at least 0.5 kg/L, more preferably 0.6 to 0.9 kg/L, and further more preferably 0.65 to 0.85 kg/L. When the packing density is 0.5 kg/L or more, ethylene oxide can be produced in high efficiency and high selectivity. It should be noted that, as a value of the packing density of the catalyst, the value of the packing density calculated by measuring packed mass of the catalyst and the length of the catalyst packed layer, in packing the catalyst in a reaction tube having a desired inner diameter, and calculating the value by the following formula (5) is adopted.

Packing density (kg/L)=Packed mass of the catalyst (kg)/Packed volume of the catalyst (L) (5)

A working method to pack the catalyst for the production of ethylene oxide in a reaction tube having a prescribed inner diameter of the reactor for producing ethylene oxide is not particularly limited, and known packing methods, for example, a method using a packing machine, a method using a template, a method of packing by manual work for each reaction tube, and the like can be used. In this regard, however, when the catalyst is packed in a reaction tube of a multi-tube type reactor for the production of ethylene oxide, it is preferable to keep packing rate at a constant rate for every tube, because silver, content in the catalyst layer and pressure loss for each reaction tube can be controlled at a value in a certain range.

The method for the production of ethylene oxide of this invention can be carried out according to the common method except that the catalyst for the production of ethylene oxide of this invention is used. Preferably, a method in which ethylene is subjected to catalytic vapor phase oxidation with a molecular oxygen-containing gas such as air, oxygen, oxygen-enriched air can be used.

For example, general condition in an industrial production scale, that is, a reaction temperature of 150 to 300° C., preferably 180 to 280° C., a reaction pressure of 0.2 to 4.0 MPaG, preferably 1.0 to 3.0 MPaG, a space velocity of 1,000 to 30,000 hr$^{-1}$ (STP), preferably 3,000 to 8,000 hr$^{-1}$ (STP) is adopted. Raw material gas to be contacted with the catalyst includes the one which is composed of 0.5 to 40% by volume of ethylene, 3 to 10% by volume of oxygen, 0.5 to 20% by volume of carbon dioxide, and the balance of inert gas such as nitrogen, argon, steam and lower hydrocarbons such as methane, ethane, and further 0.1 to 10 ppm by volume of halide such as ethylene dichloride, diphenyl chloride as a reaction inhibitor is included.

EXAMPLES

Explanation will be given on effect of this invention with reference to the following Examples and Controls. However, the technical scope of this invention should not be limited to these Examples. It should be noted that, in this Examples, measurements of various parameters were carried out by the following methods. As for a reactor for producing ethylene oxide, a multi-tube type reactor is used industrially, however, in this Examples, performance evaluation was performed using a single-tube type reactor.

<Bulk Density of the Carrier>

By packing the carrier into a 1 L measuring cylinder (inner diameter: 66 mm) at a rate of 2 L/min up to a marked 1 L gauge line to measure the mass and calculated the bulk density of the carrier by the following formula (6).

Bulk density (kg/L)=Packed mass of the carrier (kg)/1 (L) (6)

<Specific Surface Area of the Carrier>

After pulverizing the carrier, about 0.2 g of a classified substance to a particle diameter of 0.85 to 1.2 mm was precisely weighed. The weighed sample was deaerated at 200° C. for at least 30 minutes to measure the specific surface area by the B.E.T. (Brunauer-Emmert-Teller) method.

<Water Absorption of the Carrier>

Water absorption of the carrier was measured by the following method in accordance with the method described in Japanese Industrial Standards (JIS R 2205 (fiscal 1998)).

a) The carrier before crushing was placed in a drier maintained at 120° C. to weigh mass when constant mass was reached (dry weight: W1 (g)).

b) The carrier weighed in the above a) was immersed into water, and after boiling for 30 minutes or longer, the carrier was cooled in water at room temperature to obtain a sample saturated with water.

c) The sample saturated with water obtained in the above b) was taken out from water, wiped the surface quickly with a wet cloth, and after removing water droplets, mass was weighed (weight of the sample saturated with water: W2 (g)).

d) The water absorption was calculated according to the following formula (7) using W1 and W2 obtained above.

$$\text{Water absorption (\%)} = [(W2 - W1)/W1] \times 100 \quad (7)$$

<Crush Strength of the Carrier>

Using a precise dynamograph (manufactured by Marubish Science Machine Manufacturing Co., Ltd.), crush strength from a lateral direction of the carrier (a vertical direction relative to the length) was measured, and average value of 50 pieces was adopted as the crush strength.

<Wear Rate of the Carrier>

Wear rate was measured by the following procedures.

a) 100 mL of the carrier was placed in a 300-mL conical beaker.

b) Pure water was added into the above conical beaker up to 250 mL.

c) The above b) was heated with an electric heater and boiled for 30 minutes.

d) After the boiling operation, the following operation was repeated five times: Pure water remained in the conical beaker was discharged, pure water was added newly, and only pure water was discharged.

e) Washing operation of the above b) to d) was repeated three times.

f) The carrier after washing was dried in a drier at 120° C. over night.

g) The carrier after the drying was cooled down to room temperature to perform weighing (mass before a test: W3 (g)).

h) The carrier obtained in the above g) was rotated in a ball mill made of stainless steel (outer diameter: 90 mm, height: 90 mm) at 106 rpm for 30 minutes.

i) Total amount of the carrier after the rotation was transferred on a sieve made of stainless steel (inner diameter: 150 mm, sieve mesh size: 1.7 mm) to sieve, and then weighed (mass after sieving: W4 (g)).

j) Wear rate was determined according to the following formula (8) using w3 and W4 obtained above.

$$\text{Wear rate (\%)} = [(W3 - W4)/W3] \times 100 \quad (8)$$

<Analysis Method for Silver Supporting Rate>

Silver supporting rate (% by mass) based on mass of the catalyst was measured by the following procedures.

a) Weight of a catalyst (one particle) was weighed, and placed in a 100 mL conical beaker.

b) Nitric acid was added to the above conical beaker up to 20 mL.

c) After stirring nitric acid until silver in the catalyst was completely dissolved, pure water was added up to 50 mL.

d) The above c) was heated with an electric heater and boiled for 10 minutes.

e) After the boiling operation, pure water remained in the conical beaker was collected in a 200 mL tall beaker, and pure water was added up to 100 mL.

f) Content of silver contained in the solution of the above e) was measured by an automatic potentiometric titrator (COM-1600, manufactured by Hiranuma Sangyo Corp.). It should be noted that, as a titrant, 0.1 mol/L of NaCl aqueous solution was used.

<Calculation Method for Average Silver Supporting Rate>

For 30 particles of randomly selected catalyst, silver supporting rates were measured by the above-described <Analysis method for silver supporting rate>, and an arithmetic mean of the silver supporting rates for 30 particles of the catalyst was determined.

<Relative Standard Deviation of Silver Supporting Rate>

For 30 particles of randomly selected catalyst, silver supporting rates were measured by the above-described <Analysis method for silver supporting rate>, and relative standard deviation was determined according to the above formulae (1) and (2).

<Conversion and Selectivity of the Catalyst for the Production of Ethylene Oxide>

Conversion and selectivity at the time the production of ethylene oxide is initiated and after one year were calculated according to the following formulae (9) and (10), respectively. The performance when production of ethylene oxide was initiated is referred to as "initial performance", and the performance after one year is referred to as "life performance".

$$\text{Conversion(\%)} = [(\text{Number of moles of reacted ethylene})/(\text{Number of moles of ethylene in feed gas})] \times 100 \quad (9)$$

$$\text{Selectivity(\%)} = [(\text{Number of moles of ethylene converted to ethylene oxide})/(\text{Number of moles of reacted ethylene})] \times 100 \quad (10)$$

Example 1

For 4 L of a carrier having α-alumina as a main component (8 mm ring, bulk density: 0.72 kg/L, water absorption: 41.1%, specific surface area: 1.37 m$^2$/g), boiling processing using distilled water (4 L) for 30 minutes or longer was repeated three times. After that, the carrier was sufficiently dried in a drier maintained at 120° C.

Meanwhile, into aqueous slurry containing 520 g of silver oxalate (water content in the aqueous slurry: 150 g), 100 mL of water and a solution dissolved with 3.7 g of cesium nitrate into 250 mL of water were added to obtain a sludge-like mixture. Subsequently, 250 mL of ethylenediamine was added thereto and dissolved by sufficient stirring to prepare an impregnating solution.

The resultant impregnating solution was impregnated to 2,000 g of the carrier which had been heated at about 100° C. in advance. The impregnation was carried out using a blender (inner diameter 20 cm×length 38 cm, rocking mixer manufactured by Aichi Electric Co., Ltd.) having a volume of 10 L and cylindrical shape which was capable of mixing by revolution and rocking, at number of revolutions of 8 rpm and rocking rate of 2 spm. Subsequently, the carrier after impregnation was concentrated and dried by heating, and then taken out from the blender. Then it was activated at 400° C. for 20 minutes in air stream using a hot air drier to obtain a catalyst precursor. The resultant catalyst precursor was packed in a sealing container made of stainless steel which is capable of introducing inert gas from outside, and subjected to heat treatment at a high temperature of 530° C. in catalyst layer temperature for 3 hours in an electric furnace while nitrogen gas was introduced, to prepare catalyst A for the production of ethylene oxide. Average silver supporting rate of this catalyst was 15.0% by mass and relative standard deviation of silver supporting rate was 0.021.

Catalyst A for the production of ethylene oxide was packed in a reaction tube (inner diameter: 25 mm, tube length: 7,500 mm) equipped in an external heating double-pipe type reactor made of stainless steel to form a packed layer. Subsequently, a mixed gas composed of ethylene (21% by volume), oxygen (7.5% by volume), carbon dioxide (6.5% by volume), and the balance [methane (50.5% by volume), argon (12% by volume), the balance (nitrogen, ethane, and the like) (2.5% by volume)], further containing ethylene dichloride (2.5 ppm by volume) was introduced to the relevant catalyst layer to produce ethylene oxide under the conditions of reaction pressure of 2.0 MPaG and space velocity of 5,500 $hr^{-1}$. Performance when the production of ethylene oxide was initiated (initial performance) and performance after one year (life performance) are shown in Table 1.

Example 2

Catalyst B for the production of ethylene oxide was prepared according to the same procedures as in Example 1 except that impregnation was carried out using a double corn type blender (inner diameter 27 cm×height 41 cm) having a volume of 10 L at a number of revolutions of 0.5 rpm. Average silver supporting rate of this catalyst was 15.0% by mass and relative standard deviation of silver supporting rate was 0.093. In addition, using catalyst B for the production of ethylene oxide, ethylene oxide was produced under the same conditions as in Example 1. Performance when the production of ethylene oxide was initiated (initial performance) and performance after one year (life performance) are shown in Table 1.

(Control 1)

Catalyst "a" for the production of ethylene oxide was prepared according to the same procedures as in Example 1 except that impregnation was carried out using a spherical blender (inner diameter: 27 cm) having a volume of 3-0 L at a number of revolutions of 0.1 rpm. Average silver supporting rate of this catalyst was 15.0% by mass and relative standard deviation of silver supporting rate was 0.118. In addition, using catalyst "a" for the production of ethylene oxide, ethylene oxide was produced under the same conditions as in Example 1. Performance when the production of ethylene oxide was initiated (initial performance) and performance after one year (life performance) are shown in Table 1.

TABLE 1

|  |  |  | Example | | Control |
|---|---|---|---|---|---|
|  |  |  | 1 | 2 | 1 |
| Catalyst |  |  | A | B | a |
| Carrier | Bulk density | kg/L | 0.72 | 0.72 | 0.72 |
|  | Specific surface area | $m^2/g$ | 1.37 | 1.37 | 1.37 |
|  | Water absorption | % | 41.1 | 41.1 | 41.1 |
|  | Crush strength | N | 65.2 | 65.2 | 65.2 |
|  | wear rate | % | 0.95 | 0.95 | 0.95 |
| Catalyst | Ag Average supporting rate | % by mass | 15.0 | 15.0 | 15.0 |
|  | Relative standard deviation | — | 0.021 | 0.093 | 0.118 |

TABLE 1-continued

|  |  |  | Example | | Control |
|---|---|---|---|---|---|
|  |  |  | 1 | 2 | 1 |
| Initial performance | Selectivity | % | 82.6 | 82.4 | 82.1 |
|  | Conversion | % | 10 | 10 | 10 |
|  | Reaction temperature | °C. | 242 | 243 | 245 |
| Life performance after 1 year | Selectivity | % | 82.1 | 82.0 | 91.2 |
|  | Conversion | % | 10 | 10 | 10 |
|  | Reaction temperature | °C. | 247 | 247 | 252 |

From the results shown in the above Table 1, it can be understood that catalysts A and B of this invention each having a relative standard deviation of silver supporting rate contained in each catalyst particle of 0.1 or less exhibit not only higher initial selectivity and activity but also reduction in selectivity after one year is lower compared with those of catalyst "a" having a relative standard deviation of silver supporting rate of higher than 0.1.

From the results mentioned above, it has been confirmed that, according to this invention, a catalyst for the production of ethylene oxide superior in selectivity and life performance can be provided.

This invention provides a catalyst for the production of ethylene oxide which is superior in selectivity for ethylene oxide and hence capable of producing ethylene oxide in high selectivity, and a method for the production of ethylene oxide using the catalyst for the production of ethylene oxide. By using the method of this invention, amount of ethylene as a raw material to be used can be remarkably saved and a huge economical effect can be brought in the production of ethylene oxide in a large production scale, because a high selectivity can be maintained for a long period of time.

This application is based on Japanese Patent Application No. 2010-084467 filed on Mar. 31, 2010, and the disclosure is incorporated herein by reference in its entirety.

The invention claimed is:

1. A catalyst for the production of ethylene oxide comprising silver and a reaction promoter supported on a porous carrier comprising α-alumina as a main component, characterized in that;

the relative standard deviation of the silver supporting rate on each particle of the catalyst is between 0.001 or more and 0.1 or less, indicating a variation of silver content among the catalyst particles, the value being determined by the following formula (1):

$$\text{(Relative standard deviation of silver supporting rate)} = \frac{\text{(Standard deviation of silver supporting rate)}}{\text{(Average silver supporting rate)}} \quad (1)$$

wherein the standard deviation of silver supporting rate is determined by the following formula (2):

$$\text{(Standard deviation of silver supporting rate)} = \sqrt{\frac{N \sum Xn^2 - (\sum Xn)^2}{N(N-1)}} \quad (2)$$

wherein N represents the number of catalyst particles for which the silver supporting rate is measured, N is greater than or equal to 30, and Xn represents the silver supporting rate of each particle; and the average silver supporting rate is an arithmetic mean of the silver supporting rates of N particles.

2. The catalyst for the production of ethylene oxide according to claim 1, wherein the relative standard deviation is 0.001 or more and 0.05 or less.

3. The catalyst for the production of ethylene oxide according to claim 1, wherein the average silver supporting rate is 1 to 30% by mass.

4. A method for the production of ethylene oxide which comprises subjecting ethylene to catalytic vapor phase oxidation with a molecular oxygen-containing gas in the presence of the catalyst for the production of ethylene oxide set forth in claim 1.

* * * * *